(12) United States Patent
Klemarczyk

(10) Patent No.: US 6,255,500 B1
(45) Date of Patent: Jul. 3, 2001

(54) PROCESS FOR THE EPOXIDATION OF DIENE ESTERS

(75) Inventor: Philip T. Klemarczyk, Collinsville, CT (US)

(73) Assignee: Loctite Corporation, Rocky Hill, CT (US)

( * ) Notice: Subject to any disclaimer, the term of this patent is extended or adjusted under 35 U.S.C. 154(b) by 0 days.

(21) Appl. No.: 09/488,833

(22) Filed: Jan. 21, 2000

(51) Int. Cl.$^7$ .................... C07D 301/14; C07D 301/03
(52) U.S. Cl. ............................. 549/525; 549/523
(58) Field of Search ..................... 549/525, 523

(56) References Cited

U.S. PATENT DOCUMENTS

| | | | |
|---|---|---|---|
| 5,355,580 | 10/1994 | Tsukada | 29/840 |
| 5,512,613 | 4/1996 | Afzali-Ardakani | 523/443 |
| 5,560,934 | 10/1996 | Afzali-Ardakani | 424/497 |
| 5,760,337 | 6/1998 | Iyer | 174/52.2 |
| 5,783,867 | 7/1998 | Belke, Jr. | 257/783 |
| 5,872,158 | 2/1999 | Kuczynski | 522/182 |
| 5,932,682 | 8/1999 | Buchwalter | 528/94 |
| 5,948,922 | 9/1999 | Ober | 549/547 |
| 5,973,033 | 10/1999 | Ober | 523/443 |
| 6,008,266 | 12/1999 | Kuczynski | 522/31 |

FOREIGN PATENT DOCUMENTS

WO 98/31738   7/1998   (WO) .............. C08K/5/09

*Primary Examiner*—Amelia Owens
(74) *Attorney, Agent, or Firm*—Steven C. Bauman

(57) ABSTRACT

Process for the preparation of aliphatic diene ester diepoxides comprising the steps of a) reacting an aliphalic diene ester with a peracid at a temperature at or below 15° C. in the absence of a pH control agent to epoxidize the double bonds of the diene ester; and b) isolating the epoxidized diene ester form the resulting reaction mixture.

18 Claims, No Drawings

PROCESS FOR THE EPOXIDATION OF DIENE ESTERS

BACKGROUND OF THE INVENTION

1. Field of the Invention

This invention relates to a process of the epoxidation of acid-sensitive aliphatic diene esters.

2. Brief Description of Related Technology

Recently, in the field of microelectronic applications, the need has arisen for an adhesive product to attach a microelectronic component to a circuit board, which in the event of component failure may be exposed to conditions which allow for the removal of the microelectronic component from the circuit board with relative ease. In the past, failure of such components on circuit boards, had been addressed by discarding the circuit board in its entirety—with both faulty component as well as the remaining performing components still on the board. This of course leads to waste, as well as inefficiency.

Accordingly, adhesives have been developed which have been called "reworkable"—that is, the adhesive can be subjected to heat and/or chemical treatment to permit the bond to be broken between the component and the circuit board. This allows the faulty component to be removed from the circuit board, and the new component to be laid down. By so doing, the amount of waste is greatly reduced and production efficiency increased.

Many of the adhesives used for this purpose employ an epoxide based material. See e.g., U.S. Pat. Nos. 5,512,613 and 5,560,934.

Aliphatic diene esters, from which a corresponding epoxide material may be prepared, are sensitive to acid hydrolysis and the reaction of such esters with peracid epoxidizing agents would be expected to be practical only where the reaction mixture has a neutral or basic pH.

Ordinarily, in the synthesis of epoxides from olefins which contain acid sensitive groups, a buffer is added to maintain the reaction mixture at neutral or basic pH during the epoxidation step. However, the use of such buffer, while allowing the reaction to proceed as desired, creates the need to remove the buffer after the reaction has been terminated. The removal step can often be tedious, and adds additional labor and time to the process.

Accordingly, it would be desirable to provide a method of epoxidizing epoxidizable olefinic compounds which does not require use of such a buffer.

SUMMARY OF THE INVENTION

It has now been discovered that aliphatic diene esters including cycloaliphatic diene esters which contain one or more acid sensitive groups, can be reacted with peracids in the absence of a pH control agent, e.g., an alkaline compound and/or a pH buffering agent, such as sodium carbonate or sodium bicarbonate, when the reaction temperature is maintained at or below 15° C., e.g., from −20° C. to 15° C., to give the corresponding aliphatic diepoxy ester in excellent yield and purity. The present process is moreover a simple, straightforward and relatively inexpensive process that can be carried out in large scale runs to produce commercially useful quantities of pure reaction product.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The process of the invention for the diapoxidation of acid-sensitive aliphatic diene esters includes the steps of a) reacting an acid-sensitive aliphatic diene ester with a peracid at a temperature at or below 15° C. in the absence of a pH control agent in the presence of an organic, polar solvent to epoxidize the double bonds of the diene ester; and b) isolating the epoxidized diene ester from the resulting reaction mixture.

While various aliphatic diene esters can be used in the practice of the invention, preferred aliphatic diene esters for use herein are cycloaliphatic diene esters having the following formula:

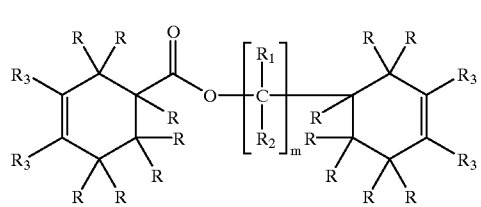

I where each R is independently selected from hydrogen, methyl, ethyl, propyl, isopropyl, butyl, isobutyl, tert butyl, $C_{1-4}$ alkoxy, halogen, cyano and nitro, and each $R_3$ is independently selected from hydrogen, methyl, ethyl, propyl, and isopropyl, $R_1$ and $R_2$ are each independently selected from hydrogen, methyl, ethyl and propyl, provided that both $R_1$ and $R_2$ cannot be hydrogen and m is 0 or 1.

The diepoxidized diene esters resulting from the epoxidation of the diene esters within formula I have the following formula:

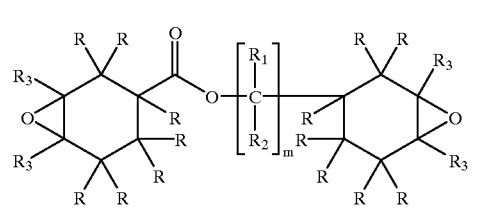

II where R, $R_1$, $R_2$, $R_3$, and m have the same meanings as given above for the diene esters within formula I. Particularly desirable compounds within formula II include the following:

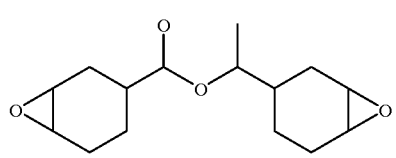

III

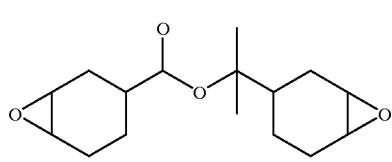

IV

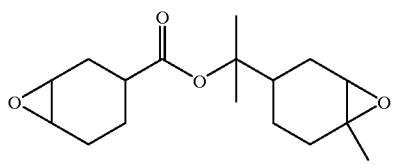

V

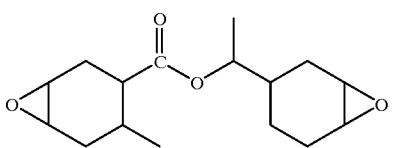

VI

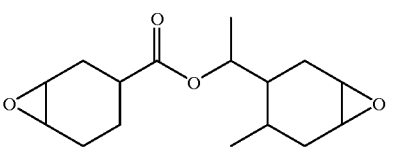

VII

The diene esters within formula I can be prepared by reacting an alcohol within formula VIII below:

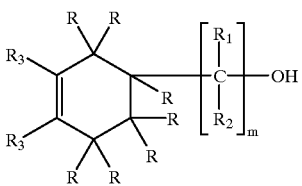

VIII where R, $R_1$, $R_2$, $R_3$ and m have the meanings given above for formula I with an acid chloride within formula IX below:

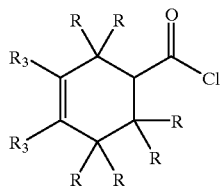

IX where R and $R_3$ have the meanings given above for formula I, in an anhydrous polar solvent at a temperature ranging from 0 to 20° C. for a time period ranging from 6 to 18 hours, to produce compounds of within formula I above.

Desirable compounds of formula I are those where m=1. Particularly desirable compounds within formula I are those where m=1, and all R groups are hydrogen.

The peracids used in step a) above are the peracids known for carrying out epoxidation reactions, such as peracetic acid, perbenzoic acid, meta-chloroperbenzoic acid, and the like.

The polar solvent used in step a) is any anhydrous organic polar solvent inert to the reactants, such as methylene chloride, chloroform, and carbon tetrachloride.

The quantities of reactants used in step a) are not critical, provided sufficient peracid is present to epoxidize both double bonds in the diene ester. In general, an excess of peracid is used, e.g., a quantity of from about 1.1 to about 1.5 equivalents of peracid per double bond in the diene ester. The reaction in step a) is carried out until epoxidization of the diene ester which usually occurs within a period of time of from 2 to 18 hours.

The reaction should be carried out by slowly adding the peracid to the diene ester in the polar solvent, e.g., over a period of from 1 to 6 hours, while maintaining the temperature at or below 15° C., e.g., from −20° C. to 15° C., more particularly from 0 to 10° C., during the addition and for an additional period of time to complete the reaction.

Step a) of the process, i.e., isolating the epoxidized diene ester from the resulting reaction mixture, can be carried out by first removing the precipitated acid by-product obtained form the peracid, e.g., by filtration. For example, if the peracid selected is m-chloroperbenzoic acid, m-chlorobenzoic acid will be obtained as a precipitate. The reaction mixture can then be washed with aqueous solutions of alkali metal sulfite, alkali metal carbonate, and water. The organic layer can then be dried, filtered, optionally treated with a basic absorbent, such as basic alumina or silica gel, to remove trace acidic impurities, and the polar solvent removed under reduced pressure. While the above technique can be used in step a), other techniques may be available to those skilled in this art, and the present invention is not limited to any particular method for isolating the reaction product from the step a) reaction mixture.

The diepoxidized diene esters prepared by the process of the invention are useful as epoxy compounds for reaction with carboxylic anhydride curing agents, together with initiators and promoters for thermal curing to provide thermosets that can be subjected to molecular disassembly (i.e., are "reworkable"), and are accordingly particularly useful for electrical insulation and for microelectronic encapsulation; allowing repair, replacement, recovery, and recycling of operative electronic components from assemblies which have become inoperative. The epoxidized diene esters, carboxylic acid anhydride curing agents, initiators and promoters may be combined together in a one part system or maintained in a two part system until desirably used, at which point the components may be mixed and the adhesive applied as desired.

The carboxylic anhydride curing agents (hardeners) are cyclic anhydrides such as hexahydrophthalic anhydride, hexahydro-4-methylphthalic anhydride, maleic anhydride, nadic methyl anhydride, cis-2-cyclohexanedicarboxylic anhydride, and the like. Of course, combinations of those hardeners may also be used.

Initiators which may be chosen for use herein, include hydroxyl functional initiators, such as high boiling alcohols or polyols, e.g., ethylene glycol, diethylene glycol, and the like. Of course, combinations of those initiator may also be used.

Promoters may be chosen for use herein, including amine promoters, such as tertiary amines, e.g., benzyldimethylamine, triethylamine, pyridine, and the like. Of course, combinations of those promoters may also be used.

The invention will be illustrated but not limited by the following examples.

EXAMPLES

Example 1

125 grams (477 mmoles) of an aliphatic diene ester of the formula

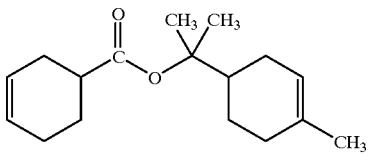

and 1000 ml of methylene chloride were added to a reaction flask, and the resulting solution cooled to about 10° C. with an ice bath. Then 259.5 grams (1050 mmoles) of 70% m-chloroperbenzoic acid was added with stirring in small increments over a period of 110 minutes, while maintaining the temperature of the reaction mixture below 15° C. during the addition. The reaction mixture was stirred overnight while maintaining the temperature below 15° C. m-Chlorobenzoic acid precipitate which formed was filtered off and the filtrate washed twice with 500 ml of 10% aqueous $Na_2SO_3$, twice with 500 ml of saturated aqueous $Na_2CO_3$ solution, and twice with 500 ml of water. The organic layer was separated, dried over $MgSO_4$, and filtered. 50 Grams of basic alumina was then added to the filtrate, the mixture stirred for 45 minutes, and filtered. The methylene chloride solvent was removed under reduced pressure and the product vacuum dried. 120.7 Grams (86% yield) of pure product of the formula was obtained.

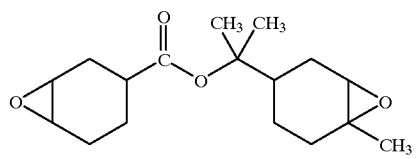

Comparative Example 1

26.2 Grams (100 mmoles) of the alphatic diene ester used in Example 1 and 250 ml of methylene chloride were added to a reaction flask, and the resulting solution cooled in an ice bath. 77.8 Grams (270 mmoles) of m-chloroperbenzoic acid was added with stirring in small increments over a period of 15 minutes, while maintaining the temperature of the reaction mixture below 30° C. (25–29° C.) during the addition. The reaction mixture was stirred overnight while allowing the temperature to become room temperature. m-Chlorobenzoic acid precipitate which formed was filtered off, and the filtrate washed twice with 250 ml of 10% aqueous $Na_2SO_3$, twice with 350 ml of saturated aqueous $NaHCO_3$ solution, and once with 250 ml of water. The organic layer was separated, dried over $MgSO_4$, and filtered. 50 Grams of basic alumina was then added to the filtrate, the mixture stirred for 45 minutes, and filtered. The methylene chloride solvent was removed under reduced pressure and the product vacuum dried. 26.5 Grams of a crude reaction product was obtained, which was shown by NMR to be significantly contaminated with an aromatic compound by-product.

What is claimed is:

1. A process for the epoxidation of acid-sensitive aliphatic diene esters, comprising the steps of a) reacting an acid-sensitive diene ester with a peracid at a temperature at or below about 15° C. in the absence of a pH control agent, to epoxidize the double bonds; and b) isolating the epoxidized diene ester from the resulting reaction mixture.

2. The process of claim 1, wherein step a) is carried out in an organic polar solvent inert to the reactants.

3. The process of claim 2, wherein the polar solvent is a member selected from the group consisting of methylene chloride, chloroform, carbon tetrachloride and combinations thereof.

4. The process of claim 1, wherein step a) is carried out under anhydrous conditions.

5. The process of claim 1, wherein the temperature in step a) is from −20° C. to 15° C.

6. The process of claim 1, wherein the temperature in step a) is from 0 to 10° C.

7. The process of claim 1, wherein the diene ester is within formula I:

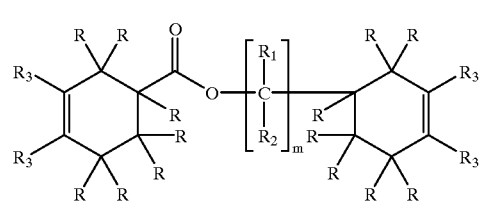

wherein each R is independently selected from hydrogen, methyl, ethyl, propyl, isopropyl, butyl, isobutyl, tert butyl, $C_{1-4}$ alkoxy, halogen, cyano and nitro, and each $R_3$ is independently selected from hydrogen, methyl, ethyl, propyl and isopropyl, $R_1$ and $R_2$ are each independently selected form hydrogen, methyl, ethyl and propyl, provided that both $R_1$ and $R_2$ cannot be hydrogen, and m is 0 or 1.

8. The process of claim 7, wherein m in formula I is 1.

9. The process of claim 7, wherein m in formula I is 1, and all R groups are hydrogen.

10. The process of claim 1, wherein the process produces a compound within formula V:

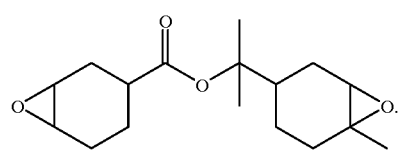

11. The process of claim 1, wherein the process produces a compound within formula VII:

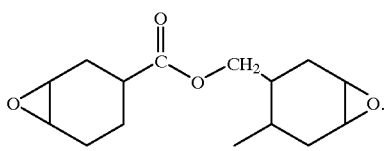

12. The process of claim 1, wherein the process produces a compound within formula III:

III

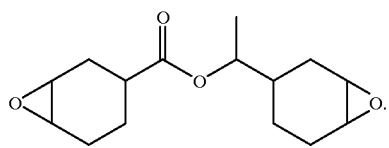

13. The process of claim 1, wherein the process produces a compound within formula IV:

IV

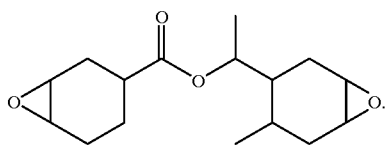

14. The process of claim 1, wherein the process produces a compound within formula VI:

VI

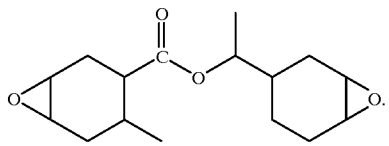

15. The process of claim 1, wherein the peracid is selected from the group consisting of peracetic acid, perbenzoic acid, m-chloroperbenzoic acid and combinations thereof.

16. A process for the epoxidation of acid-sensitive aliphatic diene esters, comprising the steps of a) reacting an acid-sensitive diene ester with a peracid at a temperature at or below 15° C. in the absence of a pH control agent in an organic polar solvent inert to the reactants to epoxidize the double bonds in the diene ester; and b) isolating the epoxidized diene ester from the resulting reaction mixture.

17. The process of claim 16, wherein the process produces a compound within formula VII:

VII

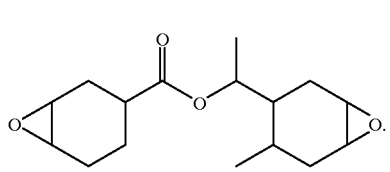

18. The process of claim 16, wherein the process produces a compound within formula V:

V

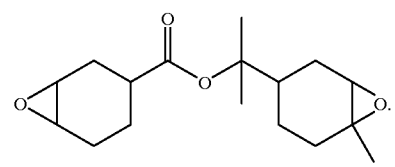

* * * * *

UNITED STATES PATENT AND TRADEMARK OFFICE
CERTIFICATE OF CORRECTION

PATENT NO. : 6,255,500 B1
DATED : July 3, 2001
INVENTOR(S) : Klemarczyk, P.

It is certified that error appears in the above-identified patent and that said Letters Patent is hereby corrected as shown below:

<u>Title page,</u>
ABSTRACT,
Lines 7-8, delete: "...diene ester form the resulting...", and insert: -- ...diene ester from the resulting... --.

<u>Column 3,</u>
Line 43, delete "

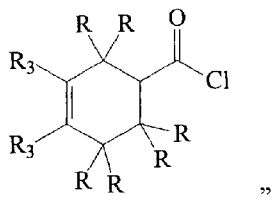

"

and insert: --

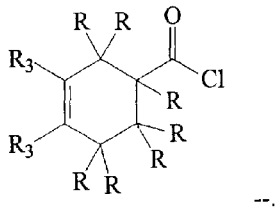

--.

Signed and Sealed this

First Day of October, 2002

Attest:

JAMES E. ROGAN
Attesting Officer
Director of the United States Patent and Trademark Office